United States Patent
Befus et al.

(10) Patent No.: US 10,942,174 B2
(45) Date of Patent: Mar. 9, 2021

(54) CALCIUM BINDING PROTEIN, SPERMATID SPECIFIC 1, AS A BIOMARKER FOR DIAGNOSIS OR TREATMENT OF STRESS

(71) Applicant: THE GOVERNORS OF THE UNIVERSITY OF ALBERTA, Edmonton (CA)

(72) Inventors: Dean Befus, Edmonton (CA); Thomas Ritz, Edmonton (CA); Chris St. Laurent, Edmonton (CA); Katherine St. Laurent, Edmonton (CA)

(73) Assignee: The Governors Of The University Of Alberta

( * ) Notice: Subject to any disclaimer, the term of this patent is extended or adjusted under 35 U.S.C. 154(b) by 116 days.

(21) Appl. No.: 16/084,617

(22) PCT Filed: Mar. 14, 2017

(86) PCT No.: PCT/CA2017/050331
§ 371 (c)(1),
(2) Date: Sep. 13, 2018

(87) PCT Pub. No.: WO2017/156625
PCT Pub. Date: Sep. 21, 2017

(65) Prior Publication Data
US 2019/0079082 A1    Mar. 14, 2019

Related U.S. Application Data

(60) Provisional application No. 62/308,655, filed on Mar. 15, 2016.

(51) Int. Cl.
*G01N 33/53* (2006.01)
*G01N 33/68* (2006.01)
*G01N 33/50* (2006.01)
*G16B 25/00* (2019.01)

(52) U.S. Cl.
CPC ..... *G01N 33/5308* (2013.01); *G01N 33/5091* (2013.01); *G01N 33/6893* (2013.01); *G16B 25/00* (2019.02); *G01N 2333/4727* (2013.01); *G01N 2800/301* (2013.01)

(58) Field of Classification Search
None
See application file for complete search history.

(56) References Cited

PUBLICATIONS

Kawashima et al, CABS1 is a novel calcium-binding protein et al, Biol. Reprod., Jun. 2009, 80(6). 1293-1304.
Calvel et al, CLPH, a novel casein kinase et al, J. Proteome Res., Jun. 2009, 8(6), 2953-2965.
Shawki et al, Identification, localization et al, Exp. Anim., 2016, 65(3), 253-265.
St. Laurent et al, Calcium binding protein et al, Am. J. Physiol. Regul. Integr. Comp. Physiol., Jan. 28, 2015 (Jan. 28, 2015), 308, R569-R575.

*Primary Examiner* — Changhwa J Cheu
(74) *Attorney, Agent, or Firm* — Kirsten M. Oates; Rodman & Rodman LLP

(57) ABSTRACT

A method of determining risk of stress in a subject involves determining in a biological sample, the level of one or more forms of calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms; comparing the level of the one or more forms in the sample with the level of the one or more forms in a normal control; determining whether the subject has risk of stress in accordance with the result; wherein a difference in the level of the one or more forms relative to the level of the normal control, is indicative of stress or responsiveness to stressful stimuli; and treating the subject with a stress management program that involves using one or more forms of 12 kDa, 15 kDa, 18 kDa, 20 kDa, 27 kDa, 33 kDa, 55 kDa, or 90 kDa forms as therapeutic targets.

15 Claims, 4 Drawing Sheets

CALCIUM BINDING PROTEIN, SPERMATID SPECIFIC 1, AS A BIOMARKER FOR DIAGNOSIS OR TREATMENT OF STRESS

CROSS-REFERENCE TO RELATED APPLICATIONS

This application claims the benefit of U.S. Provisional Patent Application Ser. No. 62/308,655, filed Mar. 15, 2016, the entirety of which is incorporated herein by reference (where permitted).

FIELD OF THE DISCLOSURE

The present invention is directed to forms of calcium binding protein spermatid specific 1 protein, and methods of using these forms of CABS1 as biomarkers for diagnosis or treatment of stress.

BACKGROUND

Saliva has been used successfully to analyze changes in hormonal, immune, and enzymatic activity related to stress in humans (Bosch, 2014; Montoya et al., 1997). Salivary free cortisol has been analyzed and increases have been demonstrated in paradigms of laboratory speech and mental challenge tasks (Hellhammer et al., 2009; Kirschbaum et al., 1993). Other studies have identified markers involved in the innate mucosal immune response, such as immunoglobulin A, mucins, lactoferrin, and cystatin S, that respond to acute laboratory stress (Ring et al., 2000; Bosch et al., 2003; Trueba et al., 2012) or more prolonged real life stress (Jemmott & Magloire, 1988; Bosch et al., 2004; McClelland et al., 1985). Markers of adaptive immune activity, such as interleukins or chemokines, have also been found secreted in saliva and altered by stressors in the laboratory (Izawa et al., 2013 Riis et al., 2015) or real life (An et al., 2015; Trueba et al., 2013). Exploration of stress-sensitive protein markers in saliva continues to evolve (Laurent et al., 2013; Trueba et al., 2012) and discovery of new markers and their function in the organisms' adaptation to challenge and adverse life conditions holds promise for improved understanding of the stress response and the development of novel interventions.

One such marker may be calcium binding protein, spermatid specific 1 (CABS1), previously also known as casein-like phosphoprotein, chromosome 4, open reading frame 35, and testis development protein NYD-SP26 identified in spermatids in selected phases of spermatogenesis and originally thought to be testis specific (Calvel et al., 2009; Kawashima et al., 2009). However, CABS1 expression was detected in human submandibular and parotid glands, and lungs, and multiple molecular weight forms of CABS1 were described, the profile of which appears to be tissue specific (St. Laurent et al., 2015). Human CABS1 contains an amino acid sequence (TDIFELL) with anti-inflammatory activities and with close homology to an anti-inflammatory sequence (TDIFEGG) identified in a related salivary gland protein, submandibular gland rat 1 (SMR1) (Mathison et al., 1997). SMR1 is a prohormone with peptide fragments that have a diversity of biological activities ranging from inhibition of inflammatory responses (Dery et al., 2004; Mathison et al., 1997; Mathison et al., 2010; Morris et al., 2007) to effects on erectile function (Messaoudi et al., 2004; Tong et al., 2006; User et al., 2003), analgesic activity (Rougeot et al., 2003) and modulation of mineral balance in tissues (Rougeot et al., 1997). SMR1 is under neuroendocrine regulation (Morris et al., 2009; Rosinski-Chupin et al., 1990; Mathison et al., 2012) and it has been postulated that its fragments and their functions are differentially regulated by autonomic and endocrine pathways.

SUMMARY

The present invention relates to forms of CABS1 protein and methods of using these forms as biomarkers for diagnosis or treatment of stress.

In one aspect, the invention comprises a method of determining risk of stress in a subject comprising:

a) determining in a biological sample, the level of one or more forms of calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms;

b) comparing the level of the one or more forms in the sample with the level of the one or more forms in a normal control;

c) determining whether the subject has risk of stress in accordance with the result of step (b); wherein a difference in the level of the one or more forms relative to the level of the normal control, is indicative of stress or responsiveness to stressful stimuli;

d) treating the subject with a stress management program.

In one embodiment, the biological sample comprises saliva.

In one embodiment, the stress comprises acute stress syndrome, post-traumatic stress syndrome, respiratory distress syndrome, acute respiratory stress syndrome, clinical stress, traumatic stress, academic stress, anxiety, depression, personality type, or coping skills.

In one embodiment, the step of determining the level of the one or more forms comprises western blotting, immunoblotting, aptamers, ELISA, or other technique. In one embodiment, the method further comprises using an extract derived from human submandibular gland as a control.

In one embodiment, the step of comparing the level of the one or more protein forms with the level of the one or more protein forms in the normal control comprises statistical analysis.

In one embodiment, the method further comprises assessing one or more parameters selected from salivary cortisol, exhaled nitric oxide, spirometric lung function, vascular endothelial growth factor, leukotriene B4, electrocardiogram, respiration, depressive mood, anxious mood, negative affect, perceived stress, asthma status, and body mass index.

In one embodiment, the method further comprises assessing the subject's response to stress treatment comprising determining the level of the one or more forms prior to treatment and after treatment, comparing the level of the one or more forms with the level of the one of more forms in a normal control, and predicting a response if there is a difference in the levels.

In one embodiment, the one or more forms comprise at least a 27 kDa protein form.

In one embodiment, the one or more forms comprise at least 12 kDa, 15 kDa, 18 kDa, 20 kDa, and 27 kDa forms.

In one embodiment, the one or more forms comprise at least 12 kDa, 15 kDa, 18 kDa, and 27 kDa forms.

In one embodiment, the one or more forms comprise at least 12 kDa, 18 kDa, and 27 kDa forms.

In one embodiment, the one or more forms comprise at least 12 kDa and 27 kDa forms.

In one embodiment, the one or more forms comprise at least 18 kDa and 27 kDa forms.

In one embodiment, the one or more forms comprise one or more of 27 kDa, 33 kDa, 50 kDa, and 90 kDa forms.

In one aspect, the invention comprises a method for analyzing for a marker indicative of stress comprising:

a) obtaining a biological sample from a subject suspected of having stress;

b) contacting the sample with a ligand for one or more forms of calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms; and c) detecting the binding of the ligand.

In one embodiment, the ligand comprises an antibody or an aptamer.

In one embodiment, the method further comprises the step of quantifying and comparing the level of the one or more forms in the sample with the level of the one or more forms in a normal control; wherein a difference in the level of the one or more forms relative to the level of the normal control, is indicative of stress or responsiveness to stressful stimuli.

In another aspect, the invention comprises a kit for detecting stress in a subject comprising:

a first reagent comprising a first ligand for one or more forms derived from calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms; and a second reagent comprising a labelled second ligand that specifically binds to the first ligand.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION

Figures 1, 2:
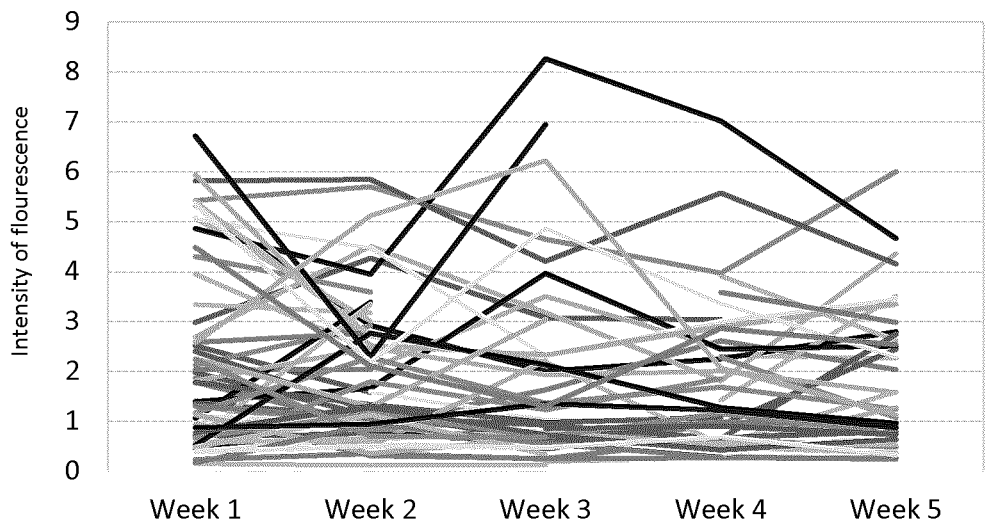
FIG. 1 is a graph showing the CABS1 band of 27 kDa (expressed as intensity of fluorescence) for individual participants across five weekly baseline assessments.
FIG. 2 is a graph showing the CABS1 band of 27 kDa (expressed as intensity of fluorescence) during the laboratory stress assessment protocol with the Trier Social Stress Test.

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a," "an," and "the" include plural referents unless the context clearly dictates otherwise.

The present invention relates to forms of calcium binding protein spermatid specific 1 protein, and methods of using the forms as biomarkers for diagnosis of stress and for its treatment.

In one embodiment, the invention comprises a method of determining risk of stress in a subject comprising:

a) determining in a biological sample, the level of one or more forms of calcium binding protein spermatid specific 1 protein (CABS1), wherein the one or more forms comprise one or more of 12 kDa, 15 kDa, 18 kDa, 20 kDa, 27 kDa, 33 kDa, 55 kDa, or 90 kDa forms;

b) comparing the level of the one or more forms in the sample with the level of the one or more forms in a normal control;

c) determining whether the subject has risk of stress in accordance with the result of step (b); wherein a difference in the level of the one or more forms relative to the level of the normal control, is indicative of stress or responsiveness to stressful stimuli; and d) treating the subject with a stress management program.

As used herein, the term "stress" refers to a physical, mental, or emotional factor which causes bodily or mental tension. The term includes external stress (for example, stress originating from an environment, psychological, or social situation) or internal stress (for example, stress originating from an illness or a medical procedure). Stress can initiate the "fight or flight" response involving a complex reaction of neurologic and endocrinologic systems. Non-limiting examples of stress include acute stress syndrome, post-traumatic stress syndrome, respiratory distress syndrome, acute respiratory stress syndrome, clinical stress, traumatic stress, academic stress, anxiety, depression, personality type, or coping skills.

As used herein, the term "subject" refers to any member of the animal kingdom. In one embodiment, a subject is a human patient. In one embodiment, a subject is an adult patient. In one embodiment, a pediatric patient is a patient under 18 years of age, while an adult patient is a patient 18 years of age or older.

As used herein, the term "calcium binding protein spermatid specific 1 protein (abbreviated as "CABS1") refers to a protein found in submandibular, other salivary glands and other tissues, including an amino acid sequence (TDIFELL) with anti-inflammatory activities and with close homology to an anti-inflammatory sequence (TDIFEGG) in submandibular gland rat 1 (abbreviated as "SMR1").

As used herein, the term "CABS1 form" or "form" refers to a protein form or portion of CABS1. The forms disclosed herein are predictive, diagnostic, and prognostic biomarkers of stress and may be of therapeutic value. As used herein, the term "biomarker" or "marker" refers to a biological molecule, such as, for example, a protein, peptide, protein form, and the like, whose presence or concentration can be detected and correlated with a known condition, such as stress. The biomarker or marker can be utilized as part of a predictive, prognostic or diagnostic process in healthy conditions or disease states, or which, alternatively, can be used in methods for identifying a useful treatment or prevention therapy.

In one embodiment, a biological sample is acquired from a subject. The sample can be of any biological tissue or fluid. In one embodiment, the sample is saliva. Additional subject information (for example, demographic data, clinical characteristics, results from other tests or indicia of stress) can be incorporated into the methods described herein in order to assess the subject for stress. Additional subject information includes, but is not limited to, age, gender, race, salivary cortisol, exhaled nitric oxide, spirometric lung function, vascular endothelial growth factor, leukotriene B4, electrocardiogram, respiration, depressive mood, anxious mood, negative affect, perceived stress, asthma status, and body mass index. As used herein, the term "assess" or "assessing" includes any form of measurement, and includes determining if an element is present or not. The terms "determining," "measuring," "evaluating," "assessing" and "assaying" can be used interchangeably and can include quantitative and/or qualitative determinations.

The CABS1 protein forms are detected in the biological sample obtained from the subject. In one embodiment, the CABS1 forms comprise one or more of 12 kDa, 15 kDa, 18 kDa, 20 kDa, 27 kDa, 33 kDa, 55 kDa, or 90 kDa forms of CABS1. In one embodiment, the CABS1 forms comprise at least a 27 kDa form of CABS1. In one embodiment, the CABS1 forms comprise at least 12 kDa, 15 kDa, 18 kDa, 20 kDa, and 27 kDa forms of CABS1. In one embodiment, the CABS1 forms comprise at least 12 kDa, 15 kDa, 18 kDa, and 27 kDa forms of CABS1. In one embodiment, the CABS1 forms comprise at least 12 kDa, 18 kDa, and 27 kDa forms of CABS1. In one embodiment, the CABS1 forms comprise at least 12 kDa and 27 kDa forms of CABS1. In one embodiment, the CABS1 forms comprise at least 18 kDa and 27 kDa forms of CABS1. In one embodiment, the CABS1 forms comprise one or more of 27 kDa, 33 kDa, 50 kDa, and 90 kDa forms of CABS1.

In one embodiment, the level of the CABS1 forms is determined. As used herein, the term "level" refers to a determined level or concentration of the CABS1 forms. The term includes a determined level or concentration of a CABS1 form as compared to a reference (for example, a control, a reference biomarker, a baseline, or the like). In one embodiment, determining the level of the CABS1 form comprises the use of western blotting, immunoblotting, aptamers, ELISA, or other technique. In one embodiment, the method further comprises using an extract derived from human submandibular gland as a control. In one embodiment, an extract derived from human submandibular gland is used as a control.

Detection of the CABS1 forms and determination of the levels of CABS1 forms are typically achieved using methods as are well known in the art. General techniques in molecular genetics and genetic engineering are described in the current editions of Molecular Cloning: A Laboratory Manual (Sambrook et al., Cold Spring Harbor); Gene Transfer Vectors for Mammalian Cells (Miller and Calos, eds.); and Current Protocols in Molecular Biology (Ausubel et al., eds., Wiley & Sons). Cell biology, protein chemistry, and antibody techniques can be found in Current Protocols in Protein Science (Colligan et al., eds.); Current Protocols in Cell Biology (Bonifacino et al., Wiley & Sons) and Current Protocols in Immunology (Colligan et al., eds., Wiley & Sons). Reagents, cloning vectors and kits for genetic manipulation are available from commercial vendors such as BioRad, Stratagene, Invitrogen, ClonTech, and Sigma-Aldrich Co. Cell culture methods are described generally in the current edition of Culture of Animal Cells: A Manual of Basic Technique (Freshney, ed., Wiley & Sons); General Techniques of Cell Culture (Harrison and Rae, Cambridge University Press); and Embryonic Stem Cells: Methods and Protocols (Turksen, ed., Human Press). Other relevant texts are Creating High Performance Culture (Aroselli, Hu. Res. Dev. Pr., 1996) and Limits to Growth (Meadows, et al., Universe Publ., 1974). Tissue culture supplies and reagents are available from commercial vendors such as Gibco/BRL, Nalgene-Nunc International, Sigma Chemical Co., and ICN Biomedicals.

Using the above described methods, the levels of the CABS1 forms are determined. The levels of the CABS1 forms in the subject are compared with the levels of CABS1 forms in a normal control. As used herein, the term "normal control" refers to a subject without stress. The levels of CABS1 forms in the normal control are used as a baseline or benchmark to compare against the levels of the CABS1 forms in a subject having a risk of stress, experiencing stress, or being monitored for the progression or treatment of stress. The comparison may be determined by statistical analysis, using methods known to one skilled in the art. In one embodiment, the statistical analysis comprises a mixed effect model, analysis of variance (ANOVA), and the like. The results from such analysis are indicative of whether or not the subject exhibits stress or responsiveness to stressful stimuli. In one embodiment, a difference in the level of the CABS1 forms relative to the level of the normal control is indicative of stress in the subject, or responsiveness to stressful stimuli.

Following a diagnosis of risk of stress or exhibiting stress, the subject may then be treated with a stress management program to treat, ameliorate, or prevent the stress. As used herein, the term "stress management" refers to an effective treatment modality or program to include pharmacologic and non-pharmacologic components for treating, ameliorating, and/or preventing stress. As used herein, the terms "treatment," "treating," "treat," and the like, refer to obtaining a desired pharmacologic and/or physiologic effect. The effect can be prophylactic in terms of completely or partially preventing stress or symptom thereof and/or can be therapeutic in terms of a partial or complete cure for stress and/or adverse effect attributable to stress. "Treatment" covers any treatment of stress in a subject, particularly in a human, and includes: (a) preventing the stress from occurring in a subject which may be predisposed to stress but has not yet been diagnosed as having it; (b) inhibiting stress, i.e., arresting its development; and (c) relieving stress, i.e., causing regression of stress and/or relieving one or more stress symptoms. "Treatment" can also encompass delivery of an agent or administration of a therapy in order to provide for a pharmacologic effect. An agonist or antagonist to one or more CABS1 forms may be utilized as treatment. Further, CABS1 may be utilized as a potential therapeutic or a target for therapy.

In one embodiment, assessment of the subject's response to stress treatment comprises determining the level of the CABS1 forms prior to treatment and after treatment, comparing the level of the CABS1 forms with the level of the CABS1 forms in a normal control, and predicting a response if there is a difference in the levels.

Embodiments of the invention include not only the above method of conducting and interpreting the results of the above tests but also include related methods, and reagents, kits, assays, and the like, for conducting the tests.

In one embodiment, the invention comprises a method for analyzing for a marker indicative of stress comprising:

a) obtaining a biological sample from a subject suspected of having stress;

b) contacting the sample with a ligand for one or more forms of calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms; and c) detecting the binding of the ligand.

As used herein, the term "ligand" refers to a molecule capable of binding to a target molecule. Non-limiting examples of ligands include antibodies and aptamers. Antibody techniques can be found in Current Protocols in Protein Science (Colligan et al., eds.); Current Protocols in Cell Biology (Bonifacino et al., Wiley & Sons) and Current Protocols in Immunology (Colligan et al., eds., Wiley & Sons). Reagents, supplies, and kits are available from commercial vendors such as BioRad, Stratagene, Invitrogen, ClonTech, Sigma-Aldrich Co., Gibco/BRL, Nalgene-Nunc International, Sigma Chemical Co., and ICN Biomedicals. Aptamers (for example, in the form of DNA, RNA, or peptide aptamers) may also be utilized since they are capable of binding to specific target molecules.

A diagnostic kit for measuring stress would have applications in several therapeutic indications including, but not limited to, acute stress syndrome, post-traumatic stress syndrome, respiratory distress syndrome (adult and neonatal), and acute respiratory distress syndrome. In addition, such kits can be used in diagnosis of clinical stress or susceptibility to stress in students, and emergency or military personnel who have or will experience traumatic events. In one embodiment, a kit for detecting stress in a subject comprises a first reagent comprising a first ligand for one or more forms of calcium binding protein spermatid specific 1 protein, wherein the one or more forms comprise one or more of 12 kDa, 15 kDa, 18 kDa, 20 kDa, 27 kDa, 33 kDa, 55 kDa, or 90 kDa forms; and a second reagent comprising a labelled second ligand that specifically binds to the first ligand. In one embodiment, the ligand is an antibody. In one embodiment, the ligand is an aptamer.

CABS1 forms "profiling" in saliva may be useful as a tool for stress detection, classification (i.e., acute or prolonged stress), diagnosis, and prognosis, since certain CABS1 forms have been found to be correlated with stress and other forms are associated with low responses to stress. Thus, in the development of one embodiment of the present invention, it was determined whether particular CABS1 forms form a signature or "barcode" which may be indicative of stress or responsiveness to stressful stimuli.

Based on preliminary studies described in the Examples, the inventors have found that a 27 kDa protein form of CABS1 in human saliva is a potential biomarker of stress. Under experimental conditions of stress, the levels of CABS1 increase in a manner analogous to cortisol. Without being bound by any theory, the existence of several forms of CABS1 associated with stress suggests that there may be several biological functions and potentially multiple pathways that regulate their production and functions.

As described in the Examples, volunteers participated across three studies with weekly baseline measures, a psychosocial laboratory speech and mental arithmetic stressor under evaluative threat, and an observation during final academic exam stress. Salivary samples were collected and analyzed for CABS1 and cortisol. Additional measures included questionnaires of perceived stress and negative affect; exhaled nitric oxide; respiration and cardiac autonomic activity (laboratory stress); spirometric lung function; and salivary and nasal chemokine activity (vascular endothelial growth factor and leukotriene B4).

Western blot analysis identified a CABS1 immunoreactive band at 27 kDa in all participants, and additional molecular weight forms in a minority of participants. Acute stress increased intensity of bands at 18, 27, and 90 kDa, and 27 kDa increases were associated with more negative affect and lower heart rate, sympathetic activity (estimated by t-wave amplitude), respiration rate, and minute ventilation. In both acute and academic stress, changes in the 27 kDa were positively associated with salivary cortisol change. The 27 kDa band was also positively associated with nasal VEGF and salivary LTB4 levels. Participants with low molecular weight CABS1 bands showed reduced habitual stress levels and negative affect in response to acute stress. The results indicate that CABS1 is readily detected in human saliva and CABS1 fragments are associated with psychological and physiological indicators of stress.

Embodiments of the present invention are described in the following Examples, which are set forth to aid in the understanding of the invention, and should not be construed to limit in any way the scope of the invention as defined in the claims which follow thereafter.

Example 1—Overview of Studies

Saliva samples were collected from participants in three studies. Study 1 included a multiple baseline study with 5 weekly assessments, to study temporal stability of CABS1 and baseline associations with questionnaire measures of negative affect. In Study 2, participants were administered a psychosocial laboratory stress-induction tool with speech and mental arithmetic stressor under evaluative threat, which allowed us to study the response of CABS1 to an acute psychosocial stressor under controlled conditions. Study 3 was an observational protocol of academic final examination stress, allowing us to examine response of CABS1 to conditions of more prolonged real-life stress. Participants in the two stress protocols participated in larger data collections focused on stress and airway inflammation in health and asthma (Ricciardolo et al., 2004; Ritz et al., 2014; Trueba et al., submitted) and the protocols included salivary cortisol measures, exhaled nitric oxide as a marker of airway inflammation. Additional chemokine markers of nasal inflammatory processes were included in one of these protocols.

Example 2—Participants

Participants were recruited mostly from the Southern Methodist University's undergraduate psychology research volunteer pool and additionally from the community for the laboratory stress study. Participants had to be free of known respiratory diseases, except for asthma in Study 2 and 3. Exclusion criteria also included self-reported current smoking and any severe heart conditions such as angina, myocardial infarction, congestive heart failure, transient ischemic attacks, or cerebrovascular accidents. Those with asthma required a physician diagnosis of their condition and no administration of oral or injected corticosteroids in the previous 6 weeks (or 3 months in Study 2).

Example 3—Collection of Saliva

Saliva samples were collected with cotton swabs (Salivettes; Sarstedt, Inc., Newton, N.C.), which participants placed in their mouth for 2 minutes. Once completed, participants placed them into individual plastic capsules. Samples were frozen at −80° C. until they were analyzed. For analyses, cotton swabs were centrifuged and collected saliva volumes were recorded to account for changes in salivary flow which may affect protein concentrations across assessments.

Example 4—Detection of CABS1 in Saliva

Salivary samples were shipped to the University of Alberta on dry ice and then stored at −20° C. until analysis. As described previously for Western blot analyses (St. Laurent et al., 2015), proteins in salivary samples were separated on polyacrylamide gels (25 µg protein lysate was loaded for each tissue), and transferred to nitrocellulose membranes (Bio-Rad Laboratories, Mississauga, ON, Canada). Prestained protein standards (Bio-Rad) were run on each gel. Membranes were blocked as previously described (St. Laurent et al., 2015) and then incubated with rabbit anti-CABS1 (immunogen was aa 184-197; DEAD-MSNYNSSIKS) primary antibody that was affinity purified with the immunogen (previously identified as H2 antibody; St. Laurent et al., 2015) at a final concentration of 3 µg/mL. Pre-immune serum from rabbit H2 was used as an isotype control and, as a blocking control, the immunizing peptide was incubated in 10× amounts (30 µg/mL) with H2 (3 µg/mL) for 18 h before applying to the membrane. Mouse anti-human β-actin was used to assess protein loading (Santa Cruz Biotechnology, 1:5000). The secondary antibody was IRDye® 800CW goat anti-rabbit (Mandel Scientific; 1:10, 000). Blots were visualized with an Odyssey imager (Li-Cor Biosciences, Lincoln, Nebr.) by scanning simultaneously at 700 and 800 nm. Odyssey software was used for molecular weight determination and quantitation of the Western blots.

To standardize quantitation of bands among Western blots, an internal control was established using a human submandibular gland extract as described in St. Laurent et al. (2015). This standard sample was run on each Western blot and all immunoreactive bands detected in saliva were normalized to the 27 kDa band from this human submandibular gland extract, and reported as relative fluorescent units (RFU). All saliva samples were run in duplicate on different days and their normalized values were averaged.

Example 5—Detection of Salivary Cortisol

Salivary cortisol concentrations were determined using a commercially available kit, Coat-A-Count cortisol kit TKCO2 (Siemens Medical Solutions Diagnostics, Los Angeles, Calif.), which had a detection limit of 0.03 µg/mL with serial dilution of the lowest calibrator standard.

Example 6—Additional Physiological Measures

Exhaled nitric oxide (FeNO) was measured with a hand-held electrochemical analyzer (NIOX mino, Aerocrine, Solna, Sweden) in accordance with American Thoracic Society Task Force (2005) guidelines. Major sources of measurable airway nitric oxide are epithelial cells in health and a variate of immune cells, including macrophages, mast cells, and eosinophils in allergic asthma (Forsythe et al., 2001; Gilchrist et al., 2004; Proud, 2005; Yoshimura et al., 2012). One exhalation was performed against a stable resistance of 50 mL for a duration of 10 s. Participants were instructed not to eat and to only drink water 2 h prior to assessments to avoid the influences by nitrate-rich foods. Exercise or heavier physical activity was also discouraged for at least 1 h before the session. Spirometric lung function was measured in Study 3 with a hand-held electronic spirometer (AM2, Jaeger/Toennies, Würzburg, Germany) as the best of three blows.

As parameters reflecting upper airway inflammatory activity, vascular endothelial growth factor (VEGF) was measured in nasal fluid and leukotriene B4 (LTB4) in nasal fluid and saliva. Collection of saliva followed the same protocol as outline above. Nasal fluid was sampled by 3 mL saline solution (0.9% sodium chloride; Teleflex Medical Inc HUD20039 ADDIPAK Unit Dose Solutions, Morrisville, N.C.) instilled into each nostril with a Intranasal Mucosal Atomization Device™ (LMA MAD Nasal™ syringe; Teleflex Medical Inc, Morrisville, N.C.). The liquid was collected in a kidney dish and transferred into small storage tubes (Roponen et al., 2003).

All collected samples were immediately stored at −80° C. Before performing the ELISA, samples were concentrated two-fold by evaporating water using an Eppendorf Vacu-Fuge attached to a Fisher Scientific Maxima Dry vacuum pump. Enzyme Immunoassay kits (Enzo Life Science, Plymouth Meeting, Pa.) were used to determine the amounts of LBT4 and VEGF. All samples were analyzed in duplicate. The detection limits of the kits were 5.6 µg/mL for LTB4 and 14.0 µg/mL for VEGF. To ensure that the increased NaCl concentration that resulted from concentrating the nasal samples did not interfere with the immune assays, control ELISA assays were performed using the standards for LTB4 provided by the assay kit. Saline was added to the samples at the same concentration that would be present after Vacu-Fuge treatment of the nasal samples.

In Study 2, the electrocardiogram and respiration were measured by respiratory inductance plethysmography (LifeShirt; Vivometrics, Ventura, Calif.) with two inductance bands for the thorax and abdomen. Signals were amplified and A/D converted with a sampling rate of 200 Hz. Bands were calibrated using a fixed volume bag (800 mL) followed by offline qualitative diagnostic calibration (Ritz & Dahme, 2006) and fixed volume calibration. A dedicated biosignal analysis program (Vivologic, Vivometrics, Ventura, Calif.) was then used to eliminate artifacts (e.g. ectopic beats, movement artifacts) and extract relevant parameters. For respiratory parameters, tidal volume ($V_T$) and total respiratory cycle time ($T_{TOT}$) were extracted and used to also calculate minute ventilation ($V'_E$). Heart rate (HR) was calculated from the distance between adjacent R-waves. The cardiac t-wave amplitude (TWA, in mV) was extracted using the ECG boundary location function (Kline et al., 1998) embedded in the AcqKnowledge biosignal analysis software package (Version 4.1; Biopac Systems, Inc., Goleta, Calif.). The TWA has been used as a surrogate measure of cardiac sympathetic cardiac activity because of its sensitivity to stimulation with isoproterenol and beta-adrenergic blockade (Cohen et al., 1983; Kirschbaum et al., 1993; Quigley & Stifter, 2006). In adults, stressful laboratory challenges typically attenuate the TWA (Heslegrave & Furedy, 1979; Kline et al., 1998; Montoya et al., 1997; Scher et al., 1984). Although measures from impedance cardiography are more common for noninvasive estimation of cardiac sympathetic activity (Sherwood et al., 1990), the implementation of this technique was not possible because of the potential for interference with the respiratory inductance plethysmography measurements. As noninvasive estimate of cardiac vagal activity, respiratory sinus arrhythmia (RSA) was extracted from fluctuations of the interbeat interval (IBI) in the time domain by the peak-valley method (Grossman et al., 1991) using the customized rsaToolbox software (Schulz et al., 2009). RSA was log-transformed to improve distributional characteristics. Because RSA is strongly influenced by the respiratory pattern (Brown et al., 1997; Hirsch & Bishop, 1981; Bernardi et al., 2000; Grossman & Taylor, 2007; Saul et al., 1989) with both longer and deeper breaths increasing RSA potentially independent of cardiac vagal activity changes, an additional within-individual correction of RSA was employed (Ritz & Dahme, 2006). Log RSA was normalized by $V_T$ (log RSA/$V_T$) and residualized for $T_{TOT}$, a strategy that has been shown to improve the estimation of cardiac vagal activity in adults (Grossman et al., 1991; Ritz, 2009; Saul et al., 1989). The grand mean of unadjusted log RSA/$V_T$ was added to the residual to obtain the respiration-corrected RSA ($RSA_c$). Results are also reported for respiration-uncorrected RSA, to allow comparison with existing literature that does not control for respiration.

Example 7—Questionnaire Measures

The Hospital Anxiety and Depression Scale (HADS) (Segerstrom & Miller, 2004) was used to assess depressive mood (HADS-D) and anxious mood (HADS-A) in the past week. Current state negative affect was assessed with the negative affect subscale of the Positive Affect Negative Affect Schedule (PANAS-NA) (Watson et al., 1988). An additional ad-hoc rating scale (0="not at all", 10 "extremely") was used to measure how much stress participants felt in the moment in Study 1. Perceived stress was assessed with the Perceived Stress Scale (PSS) (Cohen, 1988), which measures feelings of being overwhelmed and unable to cope with challenges in the past four weeks. The 10-item version was used in at the beginning of all studies, except for approximately half of the participants of Study 1 (n=30), who were administered the abbreviated 4-item version to reduce the overall burden of the assessments.

Example 8—Procedures

Study 1. For multiple baseline assessments, participants were invited for five weekly assessments over a period of 4 weeks. Day of the week and time of day (between 8 am and 6 pm) were kept constant for individual participants. In each session, participants provided saliva samples and performed measurements of FeNO. Following that, participants filled out a questionnaire battery at a computer terminal. Upon completion of the 5th visit, participants were debriefed about the purpose of the study.

Study 2. Participants attending sessions in this study were administered the Trier Social Stress Test (TSST) (Kirschbaum et al., 1993). Sessions were scheduled in the early afternoon beginning between 12 and 3 pm. Initially, participants filled in a questionnaire battery including trait measures of stress, anxiety, and depression. Following baseline assessments the participants were told that they will be asked to give a presentation, which should make a particularly good case for them as candidates for the CEO position of a major US retailer. Two "experts on presentation skills" (one male and one female confederate of the experimenter) were then introduced briefly to the participants that would evaluate the performance regarding intelligence, creativity, and body language. The participant was then given 5 minutes alone to prepare the speech. After that, the experts returned and the participant was expected to give a 5-minute speech standing in a conference room with a video camera turned on. Then, the participants were unexpectedly asked to perform a mental arithmetic task that consisted of subtracting the number 13 from the number 6,233 and to keep subtracting the remainder aloud as accurately and as fast as possible. The duration of the mental arithmetic task was 5 minutes. Throughout, the confederates were required to maintain neutral facial expression and offer no encouragement. Only simple instructions were provided to continue with the presentation or to start again from the beginning when the arithmetic task contained a mistake. Saliva samples were scheduled at 15 and 0 min pre-stress and at 0, 15, 30, and 45 min post-stress. Participants also filled in a questionnaire on momentary negative affect at these time points. Quiet sitting measures of cardiac and respiratory activity were initiated 3 minutes before saliva sampling and FeNO measurement, at 18 and 3 min pre-stress and at 12, 27 and 42 min post-stress. Additional measures during the 10 minutes of stress task performance were extracted in 2.5-minute increments, of which the last one of the mental arithmetic task was used as measure preceding the first 0 min post-stress saliva sample. For post-stress assessments, they returned to sitting posture. Participants were then fully debriefed and the experimenter explored any signs of residual distress.

Study 3. Participants provided data at three assessment points, one at a low-stress period during the term when participants had no exams or major projects, and two during the 10 days of final academic exams at the end of the term. The low-stress assessment was scheduled 2 to 6 weeks before the first final exam assessment. During the exam period, an early and a late final exam assessment were spaced approximately 5 to 7 days apart. Assessments thus captured prolonged academic pressures associated with a final exam period, rather than acute stress of an examination (Bosch et al., 2004). To control for diurnal effects, each participant was scheduled at the same time of day for all assessments. At each assessment, participants filled in a questionnaire package, followed by saliva collection and FeNO assessments. After the third session, participants were thanked and debriefed about the purpose of the study. For participants with asthma, the same instructions for discontinuation of medication were used as in Study 2.

Example 9—Data Reduction and Analyses

In Study 1 data were obtained from a total of 64 participants (51 women). Three of the participants had asthma and were excluded from the group statistics to reduce potential variability. From the remaining participants, 60 provided samples in the first and second assessment, 48 in the third assessment, 50 in the fourth assessment, and 47 in the fifth assessment. Pearson correlations were calculated to study the stability of the levels of the 27 kDa band across assessments. Study 2 and 3 involved 16 (11 women) and 19 participants (18 women), respectively (see Table 1).

TABLE 1

Characteristics of participants in the three studies of CABS1 in saliva

|  | Study 1 (N = 64) | Study 2 (N = 16) | Study 3 (N = 19) |
| --- | --- | --- | --- |
| Gender, women, n (%) | 51 (79.7) | 6 (37.5) | 18 (94.7) |
| Age, M (SD) | 20.2 (4.3) | 33.6 (15.0) | 19.8 (1.0) |
| Race, White, n (%) | 39 (61.9) | 14 (87.5) | 16 (84.2) |
| Ethnicity, Hispanic, n (%) | 10 (15.9) | 1 (6.3) | 2 (10.5) |
| Asthma, n (%) | 3 (4.7) | 10 (62.5) | 6 (31.6) |
| Asthma, n (%) women | 3 (100.0) | 4 (40.0) | 6 (100.0) |
| Asthma well controlled, n (%) | 3 (100.0) | 8 (80.0) | 5 (83.3) |
| Age of asthma onset, years M (SD) | Not available | 6.3 (6.1) | 7.8 (4.8) |
| Maintenance medication, n (%) | 0 (0.00) | 6 (60.0) | 3 (50.0) |

Mixed effects models (MEMs) were used to analyze the data since these models are intent-to-treat analyses that include all subjects, regardless of missing data. Two sets of analyses were conducted for each study. First, the longitudinal associations between the 27 kDa band and possible related predictors (including demographics, mood, lung function, and physiological measures) were examined. Research indicates that to accurately assess the longitudinal relations between variables, one must disaggregate the "between-subjects" effects from the "within-subjects" effects (Wang and Maxwell, 2015); thus, the average level of each predictor was calculated for each individual across the assessments. This average level provided the score for the between-subjects differences in the predictor. Then, for each predictor, the deviations from the average level for each individual at each assessment were calculated. These deviation scores provided the within-subjects measures of changes in the predictor over time. Both the deviation scores and the average scores for contact were included as predictors of the 27 kDa band in the MEMs. Asthma status (yes/no), age, BMI, and time as control variables were included in all analyses.

The second set of analyses examined the change in the variables over time. These analyses were performed as repeated measures ANOVAs, using MEMs to calculate the ANOVAs (which therefore retain all subjects regardless of dropout or missing data). The covariance matrix of the errors of the repeated measures was modelled as "unstructured" in all of MEMs.

Example 10—Results

Discussed below are results obtained by the inventors in connection with the experiments of Examples 1-8.
Abundance of Bands Immunoreactive to CABS1

Western Blot analysis of the saliva identified a 27 kDa band of CABS1 in each of the 99 participants of the three studies (Table 1). In 13 participants across the three studies, low abundance CABS1 immunoreactive bands below 27 kDa were also detected at 20, 18, 15 and/or 12 kDa (Table 2). The extra bands were seen in relatively greater proportion in men (20.8%) than women (10.6%) They also tended to co-occur, thus 3 women and 1 man showed both 18 and 12 kDa bands, 1 man showed bands at 18, 15 and 12 kDa, and 2 women showed all four bands 20, 18, 15 and 12 kDa. The 12 kDa band was found alone in 2 women and the 18 kDa band alone in 3 men and 1 woman. Participants with extra bands below 27 kDa mostly self-identified as White, except for one with a 12 kDa band, who was African-American and had asthma, and one with an 18 kDa band who was Hispanic and had no asthma. One of the women with all four additional bands identified as White and had asthma.

An additional 10 participants also showed bands with a higher molecular weight between 33 and 90 kDa, 6 of these were asthmatic. Proportionally, extra bands above 27 kDa were seen more in men (16.6%) than women (8%). A band at 55 kDa was most frequently seen and it co-occurred with the 90 kDa band in 5 cases (2 of these were men). One man showed all three bands at 33, 55 and 90 kDa. All participants with extra bands in this range self-identified as White, except for one African-American woman, with bands at 55 and 90 kDa.

TABLE 2

Abundance of immunoreactive bands of CABS1 in three studies, for total sample and for subsamples of women

|  | 90 kDa | 55 kDa | 33 kDa | 27 kDa | 12 kDa | 15 kDa | 18 kDa | 20 kDa | Total 12 to 20 kDa | Total 33 to 90 kDa |
| --- | --- | --- | --- | --- | --- | --- | --- | --- | --- | --- |
| Study 1 (N = 64), n (%) | 0 (0.0) | 0 (0.0) | 0 (0.0) | 64 (100.0) | 5 (7.8) | 0 (0.0) | 4 (6.3) | 0 (0.0) | 6 (9.4) | 0 (0.0) |
| women (n = 51), n (%) | 0 (0.0) | 0 (0.0) | 0 (0.0) | 51 (100.0) | 5 (9.8) | 0 (0.0) | 4 (7.8) | 0 (0.0) | 6 (11.8) | 0 (0.0) |
| Study 2 (N = 16), n (%) | 5 (31.3) | 7 (43.8) | 1 (6.3) | 16 (100.0) | 2 (12.5) | 1 (6.3) | 5 (31.3) | 0 (0.0) | 5 (31.3) | 7 (43.8) |
| women (n = 6), n (%) | 3 (18.1) | 3 (36.4) | 0 (9.1) | 6 (100.0) | 0 (0.0) | 0 (0.0) | 0 (0.0) | 0 (0.0) | 0 (0.0) | 3 (36.4) |

TABLE 2-continued

Abundance of immunoreactive bands of CABS1 in three studies, for total sample and for subsamples of women

|  | 90 kDa | 55 kDa | 33 kDa | 27 kDa | 12 kDa | 15 kDa | 18 kDa | 20 kDa | Total 12 to 20 kDa | Total 33 to 90 kDa |
|---|---|---|---|---|---|---|---|---|---|---|
| Study 3 (N = 19), n (%) | 0 (0.0) | 3 (15.8) | 0 (0.0) | 19 (100.0) | 2 (10.5) | 2 (10.5) | 2 (10.5) | 2 (10.5) | 2 (10.5) | 3 (15.8) |
| women (n = 18), n (%) | 0 (0.0) | 3 (16.7) | 0 (0.0) | 18 (100.0) | 2 (11.1) | 2 (11.1) | 2 (11.1) | 2 (10.5) | 2 (11.1) | 3 (16.7) |
| Total (N = 99), n (%) | 5 (0.5) | 10 (10.1) | 1 (0.0) | 99 (100.0) | 9 (9.1) | 3 (3.0) | 11 (11.1) | 2 (2.0) | 13 (13.1) | 10 (10.1) |
| women (n = 75), n (%) | 3 (4.0) | 6 (8.0) | 0 (0.0) | 75 (100.0) | 7 (9.3) | 2 (2.6) | 6 (8.0) | 2 (2.6) | 8 (10.6) | 6 (8.0) |

Multiple Baseline Assessments: Study 1
Temporal Consistency of CABS1 27 kDa Band Intensity Levels in Saliva The consistency of the 27 kDa band intensity (RFU normalized to the standard) in 25 μg of salivary protein between individuals was very good to fair in the range of $r_{tt}$=0.51 to 0.86 (Table 3, upper correlation matrix. This was comparable to the consistency of FeNO levels (Table 3, lower correlation matrix. Consistency of the levels did not decline for the 27 kDa band as a function of time, whereas such a decline was the case for FeNO. Intensity of the 27 kDa band across weeks did not change significantly for the sample overall, although there was some fluctuation of individual intensity levels (FIG. 1). Saliva volumes did not change significantly across time points (p=0.537).

TABLE 3

Comparison of the stability of CABS1 (27 kDa; lower half of matrix) in saliva and of fractional exhaled nitric oxide (FeNO; upper half of matrix) in the Study 1 (five weekly baseline assessments)

|  | Week 1 | Week 2 | Week 3 | Week 4 | Week 5 |
|---|---|---|---|---|---|
| Week 1 | 1 | .68 (57) | .66 (49) | .66 (50) | .54 (43) |
| Week 2 | .62 (55) | 1 | .84 (49) | .77 (49) | .70 (43) |
| Week 3 | .70 (43) | .62 (44) | 1 | .81 (42) | .77 (37) |
| Week 4 | .51 (44) | .63 (45) | .86 (37) | 1 | .78 (38) |
| Week 5 | .72 (43) | .67 (43) | .81 (35) | .66 (36) | 1 |

Note:
Pearson correlations (r) are shown;
sample n in parentheses;
all p < .001

Association of CABS1 27 kDa Band with Demographics and Negative Affect

No significant associations were found for the quantitative assessment of the 27 kDa band with age, gender, race, or ethnicity. The quantity of the 27 kDa band was positively associated with BMI (p<0.05). Participants with overall higher ratings of current stress had higher amounts of the 27 kDa band (p<0.001), as had those with higher depressive mood in the past week (HADS-D, p<0.05), and in tendency those with higher anxious mood in the past week (HADS-A, p<0.10), after controlling for age, gender, BMI, and assessment wave.

Association of CABS1 27 kDa Band with Airway Nitric Oxide

FeNO changes from week to week were positively associated with 27 kDa band changes (p<0.01), after controlling for age, gender, BMI, and assessment wave.

Acute Laboratory Stress: Study 2
Effects of Acute Stress on CABS1 Band at 27 kDa in Saliva:

MEM analysis indicated that the 27 kDa band changed significantly over pre- and post-stress assessments (p<0.01), with visible and significant increases from 0 min pre-stress to 0 min post-stress (p<0.01) and a drop at 45 min post-stress (p<0.05; FIG. 2). Saliva volume varied significantly across time, F(5,13)=3.66, p=0.028, which was probably due to higher values for the initial, 15 min pre stress measurement relative to subsequent measurements, but none of the individual time point comparisons was significant (p>0.112).

Association of CABS1 Band at 27 kDa with Demographics and Negative Affect

No significant associations were observed between the levels of the 27 kDa band and age, gender, or race/ethnicity. Changes in PANAS-NA were positively associated with changes in the levels of the 27 kDa band (p<0.01).

Association of CABS1 Band at 27 kDa with Salivary Cortisol, FeNO, and Cardiorespiratory Activity MEM analyses controlling for age, gender, BMI, and time showed higher overall 27 kDa band intensity for participants with lower HR (p<0.001). Within subjects, greater increases in the 27 kDa band were related to weaker HR increases (p<0.001), less reduction in TWA (p<0.05), slower breathing (longer $T_{TOT}$, p<0.01) and greater cortisol increases (p<0.05). (Table 4) Additionally, changes in the levels of the 27 kDa band were also positively associated with changes in self-reported negative affect (PANAS-NA) (p<0.01).

TABLE 4

Between-and within-subject associations of the CABS1 27 kDa band with other physiological parameters and the negative affect rating, and time effects of parameters across the Trier Social Stress Test (Study 2)

|  | Time[a] | Between[b] | Within[b] |
|---|---|---|---|
| HR | −28.7*** | −0.08*** | −0.03*** |
| TWA | 0.13*** | 3.70 | 1.37* |
| RSA | 10.5* | 0.00 | 0.00 |
| RSA/$V_{Tc}$ | 8.23 | 0.01 | 0.00 |
| $T_{TOT}$ | −0.06 | 0.15 | 0.13** |
| $V_T$ | 0.03 | −0.19 | −0.15 |
| $V'_E$ | −0.81 | −0.01 | −0.03* |
| FeNO | −0.11 | 0.00 | −0.15 |

TABLE 4-continued

Between-and within-subject associations of the CABS1 27 kDa band with other physiological parameters and the negative affect rating, and time effects of parameters across the Trier Social Stress Test (Study 2)

|  | Time[a] | Between[b] | Within[b] |
|---|---|---|---|
| Salivary cortisol | −1.05 | −0.06 | 0.02* |
| PANAS-NA | −0.49** | −1.06 | 0.34** |
| PSS |  | −0.26 |  |
| 27 kDa band | −0.32** | — | — |

Figure 3:
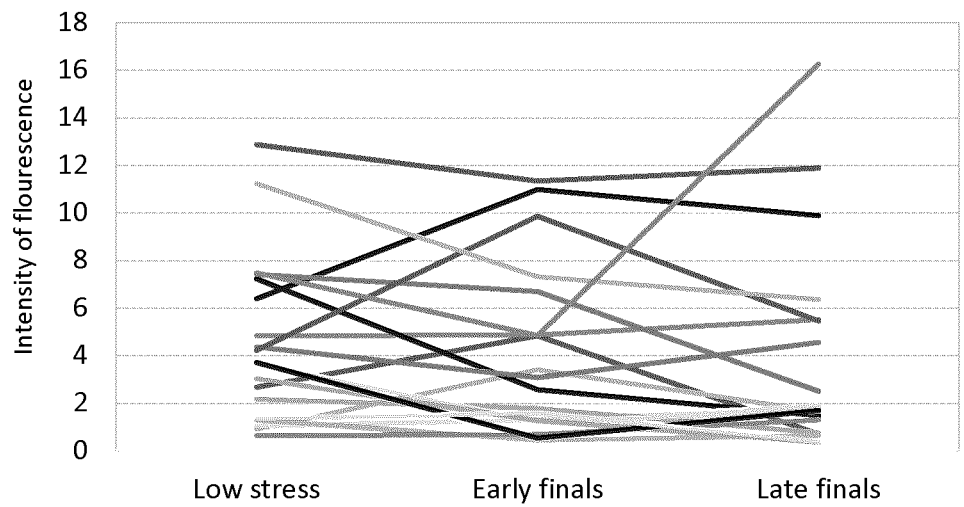
FIG. 3 is a graph showing the CABS1 band of 27 kDa (expressed as intensity of fluorescence) for individual participants during low stress and final exam stress periods.

*$p < .05$,
**$p < .01$,
***$p < .001$
[a]controlling for age and gender
[b]controlling for age, gender, and time
Note:
The results are from MLM analyses of individual parameters as single time varying covariate of the 27 kDa band; time effects are contrast of 0 min pre-stress vs. final 2.5 min of the math stressor for cardiac and respiratory indices, 0 min pre-stress vs. 0 min post-stress for FeNO, and 0 min pre-stress vs. the mean of 0, 15, 30, and 45 min post-stress for cortisol.
Abbreviations: HR, heart rate; TWA, t-wave amplitude; RSA, respiratory sinus arrhythmia; RSA/$V_{Tc}$, respiratory sinus arrhythmia normalized by tidal volume ($V_T$) and residualized by total respiratory cycle time ($T_{TOT}$); V'$_E$, minute ventilation; FeNO, fractional exhaled nitric oxide; PANAS-NA, Positive Affect Negative Affect Schedule subscale negative affect; PSS, Perceived Stress Scale Academic Exam Stress: Study 3
Effects of Final Exam Stress on CABS1 in Saliva MEM analysis with the three time points did not show any significant change in the 27 kDa band over time. Including the between-subject group variable asthma (yes/no) did not change findings. No group differences or interactions with group were found. The 27 kDa band showed a marked variability in the direction of change from low to high-stress periods (FIG. 3). Saliva volume remained stable across measurements.

Association of CABS1 27 kDa Band with Demographics, Negative Affect, and Asthma

The 27 kDa band was not substantially associated with age, gender or asthma status, but showed a marginal positive association with BMI ($p < 0.10$). Variables of negative affect were not significantly associated with the band in this sample (Table 5).

TABLE 5

Between-and within-subject associations of the CABS1 27 kDa band with other physiological parameters and the negative affect rating, and time effects of parameters, across low-stress (during term) and high-stress (early and late in finals) periods

|  | Time[a] | Between[b] | Within[b] |
|---|---|---|---|
| Salivary cortisol | 0.01 | 12.1** | 3.74* |
| FeNO | −0.06+ | 0.09 | 1.77 |
| FEV$_1$ | −6.08*** | −0.03 | −0.00 |
| Nasal VEGF | 33.0* | 0.04* | 0.00 |
| Nasal LTB4 | −0.63* | 0.75 | 0.27 |
| Salivary LTB4 | −18.25 | 0.008* | 0.00 |
| PANAS-NA | 1.61*** | −0.20 | −0.04 |
| PSS |  | −0.15 |  |
| WURSS-21 | 0.15 | −0.02 | −0.02 |
| 27 kDa band | −0.32 |  |  |

+$p < .10$,
*$p < .05$,
**$p < .01$,
***$p < .001$
[a]controlling for group, age, and BMI
[b]controlling for group, age, BMI, and time
Note:
The results are from MLM analyses of individual parameters as single time varying covariate of the quantity of the 27 kDa band; time effects are linear trends from baseline to early to late final period, except for FeNO, which is contrast of baseline vs. early and late final period; negative signs indicate decreases, and positive signs indicate increases, of the respective parameter during final periods relative to baseline
Abbreviations: see Table 4; FEV$_1$, forced expiratory volume in the first second; VEGF, vascular endothelial growth factor; LTB4, leukotriene B4; WURSS-21, Wisconsin Upper Respiratory Symptom Scale 21

Association of CABS1 27 kDa Band with Salivary Cortisol and FEV$_1$

The levels of the 27 kDa band were positively and significantly associated with levels of cortisol both between ($p < 0.01$) and within ($p < 0.05$) subjects, after controlling for group, age, BMI, and time (Table 5). Thus, participants with higher overall levels of cortisol had higher 27 kDa band values, and changes in cortisol from low-stress to high-stress exam periods were also positively associated with changes in the 27 kDa band. No association was found between CABS1 in saliva and with FEV$_1$.

Association of CABS1 27 kDa Band with Inflammatory Markers

FeNO increases within subjects were associated positively and in tendency ($p < 0.10$) with the 27 kDa band, but adding time as a covariate eliminated the effect. Between subjects, higher levels of salivary LTB4 and nasal VEGF across assessments were associated with higher levels of the 27 kDa band ($p < 0.05$) (Table 5).

Exploratory Analyses of Additional Immunoreactive Bands in the Three Studies

Figure 4:
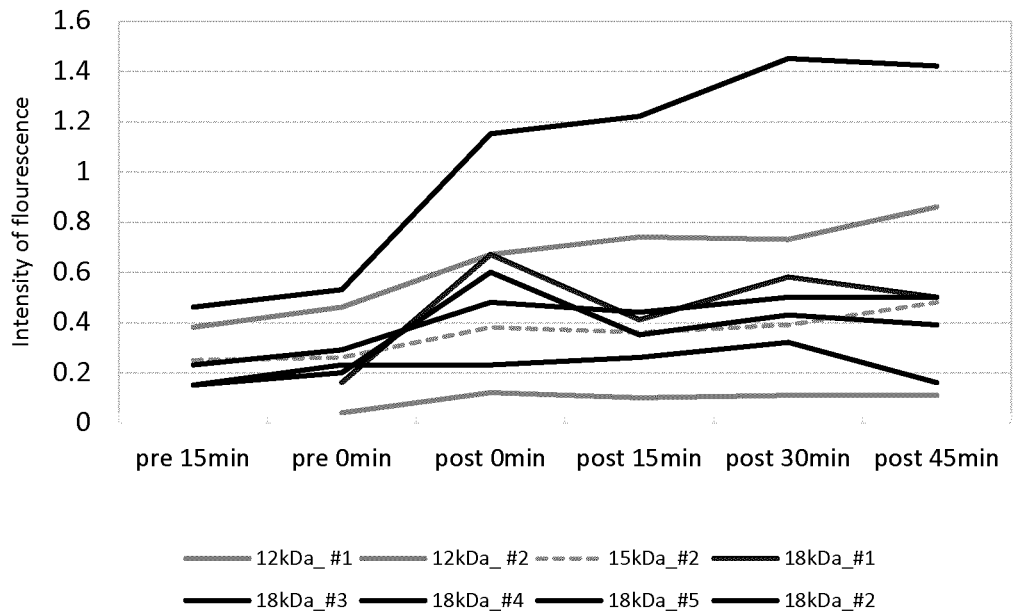
FIG. 4 is a graph showing the effects of the Trier Social Stress Test on levels of CABS1 bands of 18, 15 and 12 kDa (expressed as intensity of fluorescence) for five individual participants.
Figure 5A:
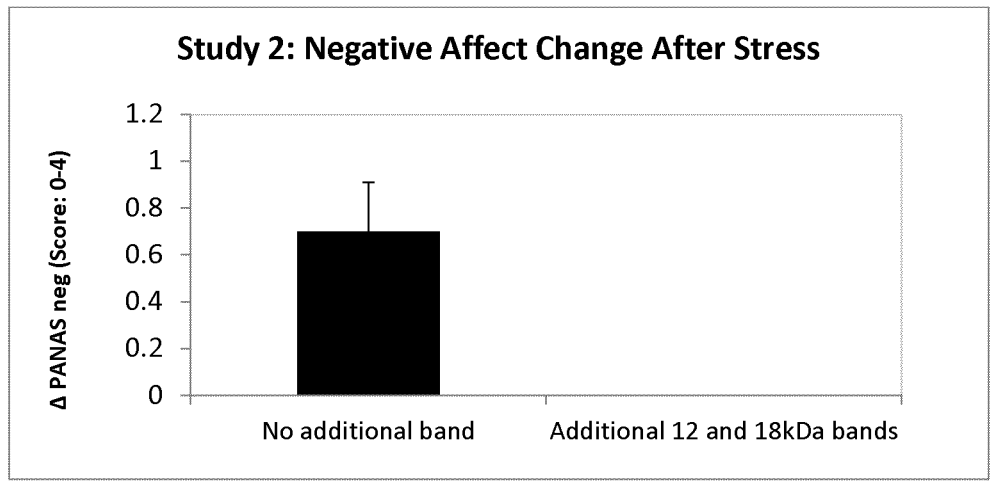
FIGS. 5A-C are graphs showing changes in negative affect (Positive Affect Negative Affect Schedule [PANAS] negative affect scale) in response to the Trier Social Stress Test in those with (n=5) and without (n=11) additional CABS1 bands at 18, 15 and/or 12 kDa (FIG. 5A); perceived Stress Scale scores in those with (n=6) and without (n=24) additional CABS1 bands at 18 and/or 12 kDa (FIG. 5B), perceived Stress Scale scores in those with (n=5) and without (n=11) additional CABS1 bands at 18, 15, and/or 12 kDa (FIG. 5C).

Because only few participants showed additional bands immunoreactive to CABS1 beyond the 27 kDa band, analysis of these bands were highly exploratory. The 18 kDa band in five participants of Study 2 showed a substantial increase following the stress test (FIG. 4), with significant time effect in the MEM analysis, $F(5,19)=7.31$, $p<0.001$, and significant elevations in levels from 0 min pre-stress to 0 min post-stress ($p<0.001$) and 30 min post-stress ($p=0.029$). These participants showed no change in PANAS-NA from 0 min pre-stress to 0 min post-stress compared to the remaining 11 participants who showed increases PANAS-NA, but lacked the additional bands, Mann-Whitney $U=0.00$, $p<0.001$, (FIG. 5A; note that U was zero because there was no overlap in ranks between both groups). Significant increases following the laboratory stressor were also observed in 7 participants who showed a 55 kDa band, $F(5,28)=3.37$, $p=0.017$, with significant elevations from 0 min pre-stress to 0 min post-stress ($p<0.001$). However, participants with this band did not differ in their PANAS-NA response from those without the band. Elevations after stress were also observed in the 90 kDa band (n=5 participants), but no significant time effect emerged ($p=0.333$).

In Study 3, although only 2 participants showed additional CABS1 bands, the abundance of the 20, 18, 15 and 12 kDa molecular forms was elevated at the late exam stress time (5 to 60 fold), compared to the baseline or early exam stress period.

Figure 5B:
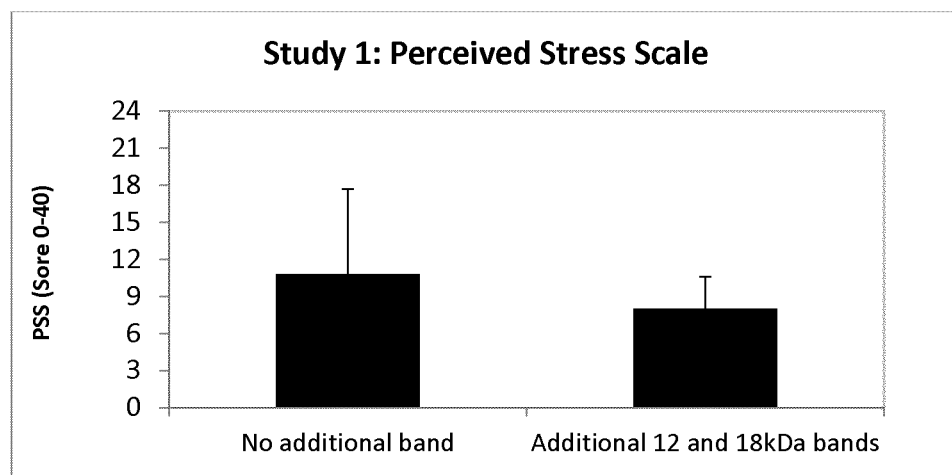
Figure 5C:
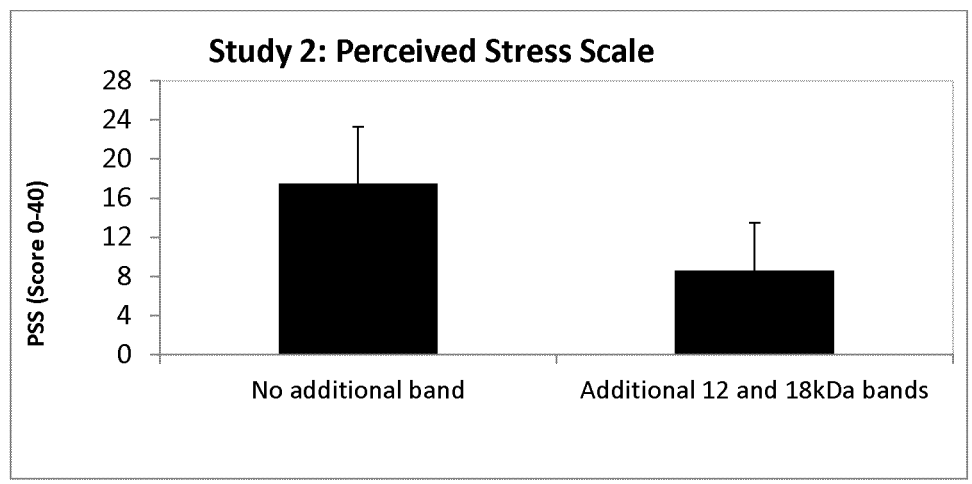

Participants with additional bands at molecular weights 12 to 18 kDa showed significantly lower values in the PSS in Study 2, $U=7.0$, $p=0.018$ ($n_1=5$, mdn=5, $n_2=11$, mdn=16) and a trend towards lower values in the second wave of Study 1, $U=36.5$, $p=0.065$ ($n_1=6$, mdn=7.5, $n_2=24$, mdn=11) (FIG. 5B, 5C) (no subjects of those receiving the 10-item version of the PSS in Study 1 showed additional bands). Participants with additional bands at molecular weights 33 to 90 kDa did not show significantly lower values in PSS than those without these bands.

Example 11—Discussion of Results from Example 10

The above studies provide the first description of the association of CABS1 in human saliva with psychological stress and inflammation. The findings suggest that CABS1 can be readily detected in human saliva and that its levels vary systematically with stress and inflammation. The predominant molecular form of CABS1 was detected at 27 kDa and additional immunoreactive bands were also identified between 12 and 20 kDa and between 33 and 90 kDa in a small (13/99 and 10/99, respectively) number of participants.

CABS1 was originally identified in human salivary gland extracts (St. Laurent et al., 2015) during the inventors' search for a human protein with a sequence similarity to the anti-inflammatory peptide sequence near the carboxy terminus of the rat prohormone, SMR1 (Mathison et al., 1997; Mathison et al., 2010; Morris et al., 2007). The Smr1 gene in rats is not present in humans and, although sequence similarity for other peptides derived from Smr1 with analgesic or erectile function activities had been identified in human PROL1 and SMR3A and SMR3B genes (Tong et al., 2007; Tong et al., 2008; Wisner et al., 2006), the human gene with a sequence similar to the anti-inflammatory sequence from Smr1 was unknown. Interestingly, just as SMR1 has many molecular form that vary in size and pI (Morris et al., 2009), using Western blot analyses and five different anti-CABS1 antibodies led to the identification of several molecular forms of CABS1 in salivary gland extracts, lungs and testes, with evidence for organ-specific differences in the forms. Mass spectrometry confirmed the presence of CABS1 sequences in bands at 75, 51, 33, 27, 20, and 16 kDa from a CABS1 overexpression lysate (St. Laurent et al., 2015). The predicted molecular size of human CABS1 is 43 kDa, a size inconsistent with any of the bands identified. The mass spectrometry data suggested that both the 75 and 51 kDa forms represent full length CABS1 (good sequence coverage 69-73%), but could provide no explanation for the two molecular weight forms. Interestingly, others have similar observations, with CABS1 from rat testes at 79 kDa (Calvel et al., 2009) and from mouse testes at 66 kDa (Kawashima et al., 2009). CABS1 immunoreactive bands below 51 kDa presumably represent fragments of full length CABS1.

The results indicate that there are several CABS1 molecular forms in human saliva. The 27 kDa form was present in the saliva from all participants and aligns well with 27 kDa in extracts of human salivary glands, lung and testes (St. Laurent et al., 2015). Without being bound by any theory, it is likely that all these molecular forms in saliva have CABS1 sequences, i.e., are modifications of CABS1. Interestingly, the molecular weight forms of CABS1 at 20 kDa and below were seen only in 13% of participants and relatively more in males (20.8 vs. 10.6%). Similarly, CABS1 forms at 33 kDa and above were seen more often in men (16.6%) vs. women (8.0%).

Analyzing the levels of these CABS1 bands in saliva in response to standardized psychological stress induction and their association with real-life stress, as well as common questionnaire measures of distress generated some intriguing findings. In general, findings suggest a sensitivity of CABS1 to acute stress and an association with self-report of perceived stress and depressive mood. Intensity of the 27 kDa band significantly increased following the laboratory psychosocial stress paradigm. On the other hand, no systematic changes were observed across periods of longer lasting stress in our observational paradigm of academic finals stress. However, the variability of the 27 kDa band in the latter paradigm was considerable, with some individuals showing pronounced increases, other decreases, and others showing very little change. Without being bound by any theory, it is possible that in longer real-life observational periods, additional moderator variables become more relevant that were not captured by our assessment protocols, such as individual coping resources or factors of changing environmental demand. Interestingly, greater increases in 27 kDa band intensity were associated with greater increases in cortisol in both the laboratory acute stress and chronic academic final examination protocols, suggesting an association with hypothalamus-pituitary adrenal (HPA) axis functioning across different types of psychological stress. The observed between-subject association of salivary cortisol levels across assessments of the academic finals stress paradigm further support a link with HPA function. Whether these correlational findings represent any correspondence in underlying physiological process remains to be explored. Interestingly, the pattern of associations with autonomic and respiratory function across the acute stress protocol suggested an involvement in system deactivation rather than activation. Increases in 27 kDa band intensity were linked to slower breathing with reduced minute ventilation, reduced heart rate, and larger t-wave amplitudes suggestive of a reduced cardiac sympathetic activation. At the same time, no association was observed with RSA as indices of cardiac parasympathetic function. It therefore appears that CABS1 is related to an attenuated cardiorespiratory response to acute stress through dampening of sympathetic excitation. Because rat SMR1 secretion is regulated by both branches of the autonomic nervous system (Morris et al., 2009), with larger quantities of protein secreted in sympathetic stimulation, it is possible that the observed associations with human CABS1 may more closely reflect the effective outcome of CABS 1 secretion on the autonomic and respiratory systems than the coordination of its initial secretion in response to stress. One function of CABS1 may be the dampening of acute stress responses, consistent with the interpretation that regulation of SMR1, the rat analog of CABS, may serve as a pathway in the organism's protective responses, including anti-inflammatory and analgesic activities, following a variety of insults (Morris et al., 2009). Protocols with more frequent collection of saliva samples throughout stress periods or direct manipulation of the CABS1 pathway will be needed to determine the exact temporal trajectories of CABS1 secretion relative to changes in autonomic excitation.

Another interesting finding with the 27 kDa band of CABS1 was its systematic association with self-reported distress. Positive associations were found with changes in momentary affect across the acute stress protocol, with momentary stress level ratings across multiple baseline assessments, and with questionnaires of perceived stress and depression in the past week(s). These findings are compatible with CABS1 upregulation during acute stress but complicate the interpretation of CABS1 associations with autonomic and respiratory parameters in acute stress. Thus, while it appears that distress experience increases the CABS1 27 kDa band with some consistency, physiological concomitants are only partly compatible with such stress-induced increases. Perhaps the multiple molecular forms of CABS1 have distinct functions that will help explain some of the complexities.

The observational protocol of academic finals stress enabled the inventors to study CABS1 relative to slower developing inflammatory processes. Consistent with a role of SMR1 in inflammation demonstrated in previous studies in animal models (Mathison et al., 1997; Dery et al., 2004; Morris et al., 2007), the inventors expected to find positive associations of CABS1 with indicators of inflammation in nasal and lower airway passages, as suggested by the positive association with FeNO changes across multiple baselines and nasal VEGF in the academic stress study (Study 3). Similarly, salivary LTB4 levels also showed a positive association with the 27 kDa band and a tendency towards higher intensities in this band was also found for participants with asthma in one study. Both LTB4 and VEGF are mediators involved in inflammation and airway infection, orchestrating leukocyte traffic to infected sites and enhancing vessel growth to support increased perfusion.

The additional immunoreactive bands of CABS1 at molecular weights 12 to 20 kDa also showed evidence for responsivity to stress, with 18 kDa in particular showing strong elevations following the acute laboratory stressor. However, different from the associations uncovered for the ubiquitous 27 kDa band, presence of this band was associated with psychological unresponsiveness to acute stress, since no change in negative affect from before to after the stressor was observed in participants with this band. Additionally, in Studies 1 and 2, values of the PSS, a measure capturing perceived stress levels retrospectively over the past weeks, were lower in those with the 18 and 12 kDa bands than in those without additional bands. The differences were particularly pronounced in Study 2 that used a longer version of the PSS, in that scores of participants with the additional bands were less than half of those of the other participants. Without being bound by any theory, it is therefore possible that additional bands provide a marker of stress resilience. The interpretation is compatible with the pattern of cardiorespiratory deactivation associated with the 27 kDa band observed in the acute stress protocol, but it is at odds with the significant positive associations observed for this band with self-report measures of distress. It is possible that different molecular forms of CABS1 yield functionally diverging effects. Unfortunately, these observations were limited by the small number of individuals that showed the additional bands and must await replication in larger studies.

Despite these limitations, the inventors' findings provide first evidence for the importance of psychological distress in the regulation of CABS1 and its various molecular weight forms in saliva. Although associations with both endocrine, autonomic, and immune function were observed, they were modest in size and could indicate an independent role of salivary CABS1 in adaptation of the organism to a stressful environment.

It should be apparent, however, to those skilled in the art that many more modifications besides those already described are possible without departing from the inventive concepts herein. The inventive subject matter, therefore, is not to be restricted except in the scope of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

All publications mentioned are incorporated herein by reference (where permitted) to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Alkon, A., Lippert, S., Vujan, N., Rodriquez, M. E., Boyce, W. T., & Eskenazi, B. (2006). The ontogeny of autonomic measures in 6- and 12-month-old infants. *Developmental Psychobiology,* 48(3), 197-208.

Allen, M. T., Fahrenberg, J., Kelsey, R. M., Lovallo, W. R., & Doornen, L. J. (1990). Methodological guidelines for impedance cardiography. *Psychophysiology,* 27(1), 1-23.

American Thoracic Society, & European Respiratory Society. (2005). ATS/ERS recommendations for standardized procedures for the online and offline measurement of exhaled lower respiratory nitric oxide and nasal nitric oxide, 2005. *American Journal of Respiratory and Critical Care Medicine,* 171(8), 912-930. doi:171/8/912

An, K., Salyer, J., & Kao, H. F. (2015). Psychological strains, salivary biomarkers, and risks for coronary heart disease among hurricane survivors. *Biological Research for Nursing,* 17(3), 311-320.

Bernardi, L., Wdowczyk-Szulc, J., Valenti, C., Castoldi, S., Passino, C., Spadacini, G., et al. (2000). Effects of controlled breathing, mental activity and mental stress with or without verbalization on heart rate variability. *Journal of the American College of Cardiology,* 35(6), 1462-1469.

Bjelland, I., Dahl, A. A., Haug, T. T., & Neckelmann, D. (2002). The validity of the hospital anxiety and depression scale: An updated literature review. *Journal of Psychosomatic Research,* 52(2), 69-77.

Bosch, J. A., de Geus, E. J., Veerman, E. C., Hoogstraten, J., & Amerongen, A. V. N. (2003). Innate secretory immunity in response to laboratory stressors that evoke distinct patterns of cardiac autonomic activity. *Psychosomatic Medicine,* 65(2), 245-258.

Bosch, J. A., Ring, C., & Amerongen, A. V. N. (2004). Academic examinations and immunity: Academic stress or examination stress? *Psychosomatic Medicine,* 66(4), 625-626.

Bosch, J. A., Ring, C., de Geus, E. J., Veerman, E. C., & Amerongen, A. V. N. (2002). Stress and secretory immunity. *Neurobiology of the Immune System,* 52, 213-253.

Bosch, J. A. (2014). The use of saliva markers in psychobiology: Mechanisms and methods. *Monographs in Oral Science,* 24, 99-108.

Brown, T. E., Beightol, L. A., Koh, J., Eckberg, D. L. (2003). Important influence of respiration on human R-R interval power spectra is largely ignored. *Journal of Applied Physiology,* 75, 2310-2317.

Bunnell, D. E., Bevier, W. C., & Horvath, S. M. (1985). Effects of exhaustive submaximal exercise on cardiovascular function during sleep. *Journal of Applied Physiology* (Bethesda, Md.: 1985), 58(6), 1909-1913.

Calvel, P., Kervarrec, C., Lavigne, R., Vallet-Erdtmann, V., Guerrois, M., Rolland, A. D., et al. (2009). CLPH, a novel casein kinase 2-phosphorylated disordered protein, is specifically associated with postmeiotic germ cells in rat spermatogenesis. *Journal of Proteome Research,* 8(6), 2953-2965.

Chen, E., Hanson, M. D., Paterson, L. Q., Griffin, M. J., Walker, H. A., & Miller, G. E. (2006). Socioeconomic status and inflammatory processes in childhood asthma: The role of psychological stress. *Journal of Allergy and Clinical Immunology,* 117(5), 1014-1020.

Chrapko, W. E., Jurasz, P., Radomski, M. W., Lara, N., Archer, S. L., & Le Mellédo, J. (2004). Decreased platelet nitric oxide synthase activity and plasma nitric oxide metabolites in major depressive disorder. *Biological Psychiatry*, 56(2), 129-134.

Cohen, S. (1988). Perceived stress in a probability sample of the United States. To finish?

Cohen, S., Kamarck, T., & Mermelstein, R. (1983). A global measure of perceived stress. *Journal of Health and Social Behavior*, 385-396.

Contrada, R. J., Krantz, D. S., Durel, L. A., Levy, L., LaRiccia, P. J., Anderson, J. R., et al. (1989). Effects of Beta-Adrenergic activity on T-Wave amplitude. *Psychophysiology*, 26(4), 488-492.

Crawford, J., Henry, J., Crombie, C., & Taylor, E. (2001). Normative data for the HADS from a large non-clinical sample. *British Journal of Clinical Psychology*, 40(4), 429-434.

d'Audiffret, A. C., Frisbee, S. J., Stapleton, P. A., Goodwill, A. G., Isingrini, E., & Frisbee, J. C. (2010). Depressive behavior and vascular dysfunction: A link between clinical depression and vascular disease? *Journal of Applied Physiology* (Bethesda, Md.: 1985), 108(5), 1041-1051.

Davies, K. P., Tar, M., Rougeot, C., & Melman, A. (2007). Sialorphin (the mature peptide product of Vcsa1) relaxes corporal smooth muscle tissue and increases erectile function in the ageing rat. *BJU International*, 99(2), 431-435.

Dery, R. E., Ulanova, M., Puttagunta, L., Stenton, G. R., James, D., Merani, S., et al. (2004). Frontline: Inhibition of allergen-induced pulmonary inflammation by the tripeptide feG: A mimetic of a neuro-endocrine pathway. *European Journal of Immunology*, 34(12), 3315-3325.

Esch, T., Stefano, G. B., Fricchione, G. L., & Benson, H. (2002). Stress-related diseases—a potential role for nitric oxide. *Medical Science Monitor: International Medical Journal of Experimental and Clinical Research*, 8(6), RA103-18.

Forsythe, P., Gilchrist, M., Kulka, M., & Befus, A. D. (2001). Mast cells and nitric oxide: Control of production, mechanisms of response. *International Immunopharmacology*, 1(8), 1525-1541.

Gilchrist, M., McCauley, S. D., & Befus, A. D. (2004). Expression, localization, and regulation of NOS in human mast cell lines: Effects on leukotriene production. *Blood*, 104(2), 462-469. doi:10.1182/blood-2003-08-2990.

Grossman, P., & Taylor, E. W. (2007). Toward understanding respiratory sinus arrhythmia: Relations to cardiac vagal tone, evolution and biobehavioral functions. *Biological Psychology*, 74(2), 263-285.

Grossman, P., Karemaker, J., & Wieling, W. (1991). Prediction of tonic parasympathetic cardiac control using respiratory sinus arrhythmia: the need for respiratory control. *Psychophysiology*, 28, 201-216.

Hellhammer, D. H., Wüst, S., & Kudielka, B. M. (2009). Salivary cortisol as a biomarker in stress research. *Psychoneuroendocrinology*, 34(2), 163-171.

Heslegrave, R. J., & Furedy, J. J. (1979). Sensitivities of HR and T-wave amplitude for detecting cognitive and anticipatory stress. *Physiology & Behavior*, 22(1), 17-23.

Hirsch, J. A., & Bishop, B. (1981). Respiratory sinus arrhythmia in humans: how breathing pattern modulates heart rate. *American Journal of Physiology*, 241, H620-H629.

Hoglund, C. O., Axen, J., Kemi, C., Jernelöv, S., Grunewald, J., Müller-Suur, C., et al. (2006). Changes in immune regulation in response to examination stress in atopic and healthy individuals. *Clinical & Experimental Allergy*, 36(8), 982-992.

Izawa, S., Sugaya, N., Kimura, K., Ogawa, N., Yamada, K. C., Shirotsuki, K., et al. (2013). An increase in salivary interleukin-6 level following acute psychosocial stress and its biological correlates in healthy young adults. *Biological Psychology*, 94(2), 249-254.

Jemmott, J. B., & Magloire, K. (1988). Academic stress, social support, and secretory immunoglobulin A. *Journal of Personality and Social Psychology*, 55(5), 803.

Kang, D., Coe, C. L., McCarthy, D. O., Jarjour, N. N., Kelly, E. A., Rodriguez, R. R., et al. (1997). Cytokine profiles of stimulated blood lymphocytes in asthmatic and healthy adolescents across the school year. *Journal of Interferon & Cytokine Research*, 17(8), 481-487.

Kawashima, A., Osman, B. A., Takashima, M., Kikuchi, A., Kohchi, S., Satoh, E., et al. (2009). CABS1 is a novel calcium-binding protein specifically expressed in elongate spermatids of mice. *Biology of Reproduction*, 80(6), 1293-1304.

Kirschbaum, C., Pirke, K. M., & Hellhammer, D. H. (1993). The 'trier social stress test'—a tool for investigating psychobiological stress responses in a laboratory setting. *Neuropsychobiology*, 28(1-2), 76-81.

Kline, K., Ginsburg, G., & Johnston, J. (1998). T-wave amplitude: Relationships to phasic RSA and heart period changes. *International Journal of Psychophysiology*, 29(3), 291-301.

Kullowatz, A., Rosenfield, D., Dahme, B., Magnussen, H., Kanniess, F., & Ritz, T. (2008). Stress effects on lung function in asthma are mediated by changes in airway inflammation. *Psychosomatic Medicine*, 70(4), 468-475.

Laguna, P., Jane, R., & Caminal, P. (1994). Automatic detection of wave boundaries in multilead ECG signals: Validation with the CSE database. *Computers and Biomedical Research*, 27(1), 45-60.

Lane, C., Knight, D., Burgess, S., Franklin, P., Horak, F., Legg, J., et al. (2004). Epithelial inducible nitric oxide synthase activity is the major determinant of nitric oxide concentration in exhaled breath. *Thorax*, 59(9), 757-760.

Laurent, H. K., Laurent, S. M., & Granger, D. A. (2013). Salivary nerve growth factor reactivity to acute psychosocial stress: A new frontier for stress research. *Psychosomatic Medicine*, 75(8), 744-750.

Liu, L. Y., Coe, C. L., Swenson, C. A., Kelly, E. A., Kita, H., & Busse, W. W. (2002). School examinations enhance airway inflammation to antigen challenge. *American Journal of Respiratory and Critical Care Medicine*, 165(8), 1062-1067.

Maes, M., Galecki, P., Chang, Y. S., & Berk, M. (2011). A review on the oxidative and nitrosative stress (O&NS) pathways in major depression and their possible contribution to the (neuro) degenerative processes in that illness. *Progress in Neuro-Psychopharmacology and Biological Psychiatry*, 35(3), 676-692.

Mathison, R. D., Befus, A. D., & Davison, J. S. (1997). A novel submandibular gland peptide protects against endotoxic and anaphylactic shock. *The American Journal of Physiology*, 273(3 Pt 2), R1017-23.

Mathison, R. D., Davison, J. S., Befus, A. D., & Gingerich, D. A. (2010). Salivary gland derived peptides as a new class of anti-inflammatory agents: Review of preclinical pharmacology of C-terminal peptides of SMR1 protein. *Journal of Inflammation* (London, England), 7, 49-60.

Mathison, R. D., Davison, J. S., St Laurent, C. D., & Befus, A. D. (2012). Autonomic regulation of anti-inflammatory activities from salivary glands. *Chemical Immunology and Allergy*, 98, 176-195.

McClelland, D. C., Ross, G., & Patel, V. (1985). The effect of an academic examination on salivary norepinephrine and immunoglobulin levels. *Journal of Human Stress,* 11(2), 52-59.

Messaoudi, M., Desor, D., Nejdi, A., & Rougeot, C. (2004). The endogenous androgen-regulated sialorphin modulates male rat sexual behavior. *Hormones and Behavior,* 46(5), 684-691.

Montoya, P., Brody, S., Beck, K., Veit, R., & Rau, H. (1997). Differential β- and α-adrenergic activation during psychological stress. *European Journal of Applied Physiology and Occupational Physiology,* 75(3), 256-262.

Morris K, Kuo B, Wilkinson M, Davison J S, Befus A D & Mathison R D. (2007). Vcsa1 gene peptides for the treatment of inflammatory and allergic reactions. *Recent Patents on Inflammation & Allergy Drug Discover,* 1:124-132.

Morris, K. E., St Laurent, C. D., Hoeve, R. S., Forsythe, P., Suresh, M. R., Mathison, R. D., et al. (2009). Autonomic nervous system regulates secretion of anti-inflammatory prohormone SMR1 from rat salivary glands. *American Journal of Physiology. Cell Physiology,* 296(3), C514-24.

Nater, U., & Rohleder, N. (2009). Salivary alpha-amylase as a non-invasive biomarker for the sympathetic nervous system: Current state of research. *Psychoneuroendocrinology,* 34(4), 486-496.

Nguyen, T., Woo-Park, J., Hess, M., Goins, M., Urban, P., Vaughan, J., et al. (2005). Assaying all of the nitrogen oxides in breath modifies the interpretation of exhaled nitric oxide. *Vascular Pharmacology,* 43(6), 379-384.

Oskis, A., Clow, A., Thorn, L., Loveday, C., & Hucklebridge, F. (2012). Differences between diurnal patterns of salivary cortisol and dehydroepiandrosterone in healthy female adolescents. *Stress,* 15(1), 110-114.

Phillips, A. C., Carroll, D., Evans, P., Bosch, J. A., Clow, A., Hucklebridge, F., et al. (2006). Stressful life events are associated with low secretion rates of immunoglobulin A in saliva in the middle aged and elderly. *Brain, Behavior, and Immunity,* 20(2), 191-197.

Proud, D. (2005). Nitric oxide and the common cold. *Current Opinion in Allergy and Clinical Immunology,* 5(1), 37-42.

Quigley, K. S., & Stifter, C. A. (2006). A comparative validation of sympathetic reactivity in children and adults. *Psychophysiology,* 43(4), 357-365.

Rau, H. (1991). Responses of the T-Wave amplitude as a function of active and passive tasks and Beta-Adrenergic blockade. *Psychophysiology,* 28(2), 231-239.

Ricciardolo, F. L., Sterk, P. J., Gaston, B., & Folkerts, G. (2004). Nitric oxide in health and disease of the respiratory system. *Physiological Reviews,* 84(3), 731-765.

Riis, J. L., Granger, D. A., DiPietro, J. A., Bandeen-Roche, K., & Johnson, S. B. (2015). Salivary cytokines as a minimally-invasive measure of immune functioning in young children: Correlates of individual differences and sensitivity to laboratory stress. *Developmental Psychobiology,* 57(2), 153-167.

Ring, C., Harrison, L. K., Winzer, A., Carroll, D., Drayson, M., & Kendall, M. (2000). Secretory immunoglobulin A and cardiovascular reactions to mental arithmetic, cold pressor, and exercise: Effects of alpha-adrenergic blockade. *Psychophysiology,* 37(05), 634-643.

Ritz, T. (2009). Studying noninvasive indices of vagal control: the need for respiratory control and the problem of target specificity. *Biological Psychology,* 80, 158-168.

Ritz, T., & Trueba, A. F. (2014). Airway nitric oxide and psychological processes in asthma and health: A review. *Annals of Allergy, Asthma & Immunology,* 112(4), 302-308.

Ritz, T., & Dahme, B. (2006). Implementation and interpretation of respiratory sinus arrhythmia measures in psychosomatic medicine: Practice against better evidence? *Psychosomatic Medicine,* 68(4), 617-627.

Ritz, T., Trueba, A. F., Simon, E., & Auchus, R. J. (2014). Increases in exhaled nitric oxide after acute stress: Association with measures of negative affect and depressive mood. Psychosomatic Medicine, 76, 716-725.

Roponen, M., Seuri, M., Nevalainen, A., Randell, J., & Hirvonen, M. R. (2003). Nasal lavage method in the monitoring of upper airway inflammation: seasonal and individual variation. *Inhalation Toxicology,* 15, 649-661.

Rosinski-Chupin, I., & Rougeon, F. (1990). A new member of the glutamine-rich protein gene family is characterized by the absence of internal repeats and the androgen control of its expression in the submandibular gland of rats. *The Journal of Biological Chemistry,* 265(18), 10709-10713.

Rougeot, C., Messaoudi, M., Hermitte, V., Rigault, A. G., Blisnick, T., Dugave, C., et al. (2003). Sialorphin, a natural inhibitor of rat membrane-bound neutral endopeptidase that displays analgesic activity. *Proceedings of the National Academy of Sciences of the United States of America,* 100(14), 8549-8554.

Rougeot, C., Vienet, R., Cardona, A., Le Doledec, L., Grognet, J. M., & Rougeon, F. (1997). Targets for SMR1-pentapeptide suggest a link between the circulating peptide and mineral transport. *The American Journal of Physiology,* 273(4 Pt 2), R1309-20.

Schulz S M, Ayala E, Dahme B, Ritz T. A MATLAB toolbox for correcting within-individual effects of respiration rate and tidal volume on respiratory sinus arrhythmia during variable breathing. Behav Res Methods. 2009 41(4):1121-6.

Sackner, M. A., Watson, H., Belsito, A. S., Feinerman, D., Suarez, M., Gonzalez, G., et al. (1989). Calibration of respiratory inductive plethysmograph during natural breathing. *Journal of Applied Physiology* (Bethesda, Md.: 1985), 66(1), 410-420.

Saul, J. P., Berger, R. D., Chen, M. H., Cohen, R. J. (1989). Transfer function analysis of autonomic regulation. II. Respiratory sinus arrhythmia. *American Journal of Physiology,* 256, H153-H161.

Scher, H., Furedy, J. J., & Heslegrave, R. J. (1984). Phasic T-Wave amplitude and heart rate changes as indices of mental effort and task incentive. *Psychophysiology,* 21(3), 326-333.

Segerstrom, S. C., & Miller, G. E. (2004). Psychological stress and the human immune system: A meta-analytic study of 30 years of inquiry. *Psychological Bulletin,* 130(4), 601.

Sherwood A, Allen M T, Fahrenberg J, Kelsey R M, Lovallo W R, van Doornen L J. Methodological guidelines for impedance cardiography. Psychophysiology. 1990 27(1): 1-23.

Silkoff, P. E., Erzurum, S. C., Lundberg, J. O., George, S. C., Marczin, N., Hunt, J. F., et al. (2006). ATS workshop proceedings: Exhaled nitric oxide and nitric oxide oxidative metabolism in exhaled breath condensate. *Proceedings of the American Thoracic Society,* 3(2), 131-145.

St Laurent, C. D., St Laurent, K. E., Mathison, R. D., & Befus, A. D. (2015). Calcium-binding protein, spermatid-specific 1 is expressed in human salivary glands and contains an anti-inflammatory motif. *American Journal of Physiology. Regulatory, Integrative and Comparative Physiology,* 308(7), R569-75.

Tong, Y., Tar, M., Davelman, F., Christ, G., Melman, A., & Davies, K. P. (2006). Variable coding sequence protein A1 as a marker for erectile dysfunction. *BJU International,* 98(2), 396-401.

Trueba, A. F., Mizrachi, D., Auchus, R. J., Vogel, P. D., & Ritz, T. (2012). Effects of psychosocial stress on the pattern of salivary protein release. *Physiology & Behavior,* 105(3), 841-849.

Trueba, A. F., Smith, N. B., Auchus, R. J., & Ritz, T. (2013). Academic exam stress and depressive mood are associated with reductions in exhaled nitric oxide in healthy individuals. *Biological Psychology,* 93(1), 206-212.

Trueba, A. F., Ryan, M. W., Vogel, P. D., Ritz, T. (submitted). *Effects of Academic Exam Stress on Nasal Leukotriene B4 and Vascular Endothelial Growth Factor in Asthma and Health.*

User, H. M., Zelner, D. J., McKenna, K. E., & McVary, K. T. (2003). Microarray analysis and description of SMR1 gene in rat penis in a post-radical prostatectomy model of erectile dysfunction. *The Journal of Urology,* 170(1), 298-301.

Vareille, M., Kieninger, E., Edwards, M. R., & Regamey, N. (2011). The airway epithelium: Soldier in the fight against respiratory viruses. *Clinical Microbiology Reviews,* 24(1), 210-229.

Watson, D., Clark, L. A., & Tellegen, A. (1988). Development and validation of brief measures of positive and negative affect: The PANAS scales. *Journal of Personality and Social Psychology,* 54(6), 1063.

Wisner, A., Dufour, E., Messaoudi, M., Nejdi, A., Marcel, A., Ungeheuer, M. N., & Rougeot, C. (2006). Human Opiorphin, a natural antinociceptive modulator of opioid-dependent pathways. Proceedings National Academy of Science USA, 103(47): 17979.

Yoshimura T, Moon T C, St. Laurent C D, Puttagunta L, Chung K, Wright E, et al. (2012). Expression of nitric oxide synthases in leucocytes in nasal polyps. *Annals of Allergy Asthma and Immunology.* 108:172-177.

Zigmond, A. S., & Snaith, R. P. (1983). The hospital anxiety and depression scale. *Acta Psychiatry Scandinavia,* 67(6), 361-370.

National Heart, Lung, and Blood Institute/National Asthma Education and Prevention Program (NHLBI/NAEPP). Expert panel report: Guidelines for the diagnosis and management of asthma. Full report 2007. NIH Publication No. 07-4051. National Institutes of Health, Bethesda, Md., 2007.

Global Initiative for Asthma (GINA) (2010). GINA Report, Global Strategy for Asthma Management and Prevention. Available at http://www.ginasthma.org/.

What is claimed is:

1. A method of determining stress in a subject comprising:
   a) determining in a biological sample from said subject, the level of one or more forms derived from calcium binding protein spermatid specific 1 protein, wherein the one or more forms comprise one or more of 12 kDa, 15 kDa, 18 kDa, 20 kDa, 27 kDa, or 55 kDa forms;
   b) comparing the level of the one or more forms in the sample with the level of the one or more forms in a normal control;
   c) determining whether the subject has stress in accordance with the result of step (b); wherein a difference in the level of the one or more forms relative to the level of the normal control, is indicative of stress or responsiveness to stressful stimuli; and
   d) administering an agent to said subject for treating, ameliorating, or preventing stress.

2. The method of claim 1, wherein the biological sample comprises saliva.

3. The method of claim 1, wherein the stress comprises acute stress syndrome, post-traumatic stress syndrome, respiratory distress syndrome, acute respiratory stress syndrome, clinical stress, traumatic stress, academic stress, anxiety, depression, personality type, or coping skills.

4. The method of claim 1, wherein the step of determining the level of the one or more forms comprises western blotting, immunoblotting, aptamers, ELISA, or other technique.

5. The method of claim 4, further comprising using an extract derived from human submandibular gland as a control.

6. The method of claim 1, wherein the step of comparing the level of the one or more forms with the level of the one or more forms in the normal control comprises statistical analysis.

7. The method of claim 1, further comprising assessing one or more parameters selected from salivary cortisol, exhaled nitric oxide, spirometric lung function, vascular endothelial growth factor, leukotriene B4, electrocardiogram, respiration, depressive mood, anxious mood, negative affect, perceived stress, asthma status, and body mass index.

8. The method of claim 1, further comprising assessing the subject's response to stress treatment comprising determining the level of the one or more forms prior to treatment and after treatment, comparing the level of the one or more forms with the level of the one of more forms in a normal control, and predicting a response if there is a difference in the levels.

9. The method of claim 1, wherein the one or more forms comprise at least a 27 kDa form.

10. The method of claim 1, wherein the one or more forms comprise at least 12 kDa, 15 kDa, 18 kDa, 20 kDa, and 27 kDa forms.

11. The method of claim 1, wherein the one or more forms comprise at least 12 kDa, 15 kDa, 18 kDa, and 27 kDa forms.

12. The method of claim 1, wherein the one or more forms comprise at least 12 kDa, 18 kDa, and 27 kDa forms.

13. The method of claim 1, wherein the one or more forms comprise at least 12 kDa and 27 kDa forms.

14. The method of claim 1, wherein the one or more forms comprise at least 18 kDa and 27 kDa forms.

15. The method of claim 1, wherein the one or more forms comprise one or more of 27 kDa and 50 kDa forms.

* * * * *